US00PP27126P3

(12) United States Plant Patent
Clark et al.

(10) Patent No.: US PP27,126 P3
(45) Date of Patent: Aug. 30, 2016

(54) COLEUS PLANT NAMED 'UF10-45-12'

(50) Latin Name: *Solenostemon scutellarioides*
Varietal Denomination: UF10-45-12

(71) Applicant: Florida Foundation Seed Producers, Inc., Marianna, FL (US)

(72) Inventors: David G. Clark, Gainesville, FL (US); Grayson M. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 90 days.

(21) Appl. No.: 14/120,606

(22) Filed: Jun. 6, 2014

(65) Prior Publication Data

US 2015/0359156 P1 Dec. 10, 2015

(51) Int. Cl.
*A01H 5/12* (2006.01)

(52) U.S. Cl.
USPC ..... Plt./469

(58) Field of Classification Search
USPC ..... Plt./469, 373, 263.1
See application file for complete search history.

(56) References Cited

U.S. PATENT DOCUMENTS

| | | | |
|---|---|---|---|
| PP21,585 | P2 | 12/2010 | Clark et al. |
| PP21,602 | P2 | 12/2010 | Clark et al. |
| PP23,585 | P3 | 5/2013 | Clark et al. |
| 2015/0359154 | P1 | 12/2015 | Clark et al. |

OTHER PUBLICATIONS

Buck University of Florida IFAS News. UF?IFAS approves 14 new cultivars for release Feb. 19, 2014, retrieved on Nov. 9, 2015, retrieved from the Internet at <https://news.ifas.ufl.edu/2014/02/ufifas-approves-14-new-cultivars-for-release/> 4 pp.*
U.S. Appl. No. 14/120,604, filed Jun. 6, 2014, Clark et al.

* cited by examiner

*Primary Examiner* — June Hwu
(74) *Attorney, Agent, or Firm* — Dentons US LLP

(57) ABSTRACT

'UF10-45-12' is a new coleus plant distinguished by having consistent chartreuse leaves with distinct red-magenta venation, a vigorous but compact growth habit, as disclosed herein.

3 Drawing Sheets

Latin name of the genus and species of the plant claimed: *Solenostemon scutellarioides.*

Cultivar denomination: 'UF10-45-12'.

BACKGROUND OF THE INVENTION

The invention relates to a new and distinct cultivar of coleus plant named 'UF10-45-12'. 'UF10-45-12' originated from an open pollination conducted in May-November 2009 in Gainesville, Fla. between the female coleus plant 'UF08-17-2' (unpatented) and an unknown male coleus plant. The first asexual reproduction was performed in May 2010 in Gainesville, Fla. by vegetative stem cuttings using a single seedling (see FIG. 1 for pedigree).

'UF10-45-12' has been reproduced asexually for over one year through vegetative stem cuttings and has been found to retain its distinctive characteristics through successive asexual propagations.

'UF10-45-12' has not been made publicly available more than one year prior to the filing date of this application.

When 'UF10-45-12' is compared to the female parent 'UF08-17-2', 'UF10-45-12' has large, chartreuse leaves with distinct deep red-magenta veins, while 'UF08-17-2' has smaller leaves colored deep maroon with bright yellow margins.

When 'UF10-45-12' is compared to the commercial cultivar 'Golden Dreams' 'UF11-23-31' (commercial, unpatented), both plants have chartreuse foliage with prominent red veins, but 'UF10-45-12' has more prominent and darker vein coloration across the leaf than 'Golden Dreams' 'UF11-23-31'. 'UF10-45-12' also has a vigorous but more compact growth habit with more lateral branching than 'Golden Dreams' 'UF11-23-31'.

SUMMARY OF THE INVENTION

The following are the most outstanding and distinguishing characteristics of 'UF10-45-12' when grown under normal horticultural practices in Gainesville, Fla. 'UF10-45-12' has a novel vigorous, upright, compact growth habit, late season flowering, excellent heat tolerance, and consistent chartreuse leaves with distinct red-magenta venation that are significantly different than other coleus plants. It has superior stability in foliage color in both sun and shade conditions, maintaining stable color in all conditions. It has a vigorous but compact upright growth habit with excellent lateral branching when grown as a stock plant, thus providing ample vegetative propagules for producers.

BRIEF DESCRIPTION OF THE DRAWINGS

This new coleus plant is illustrated by the accompanying photographs, which show the plant's form and foliage. The colors shown are as true as can be reasonably obtained by conventional photographic procedures.

FIG. 2—shows the growth habit, form, and foliage of the claimed plant.

FIG. 3—shows a close-up of the foliage.

DETAILED BOTANICAL DESCRIPTION

Figure 1:
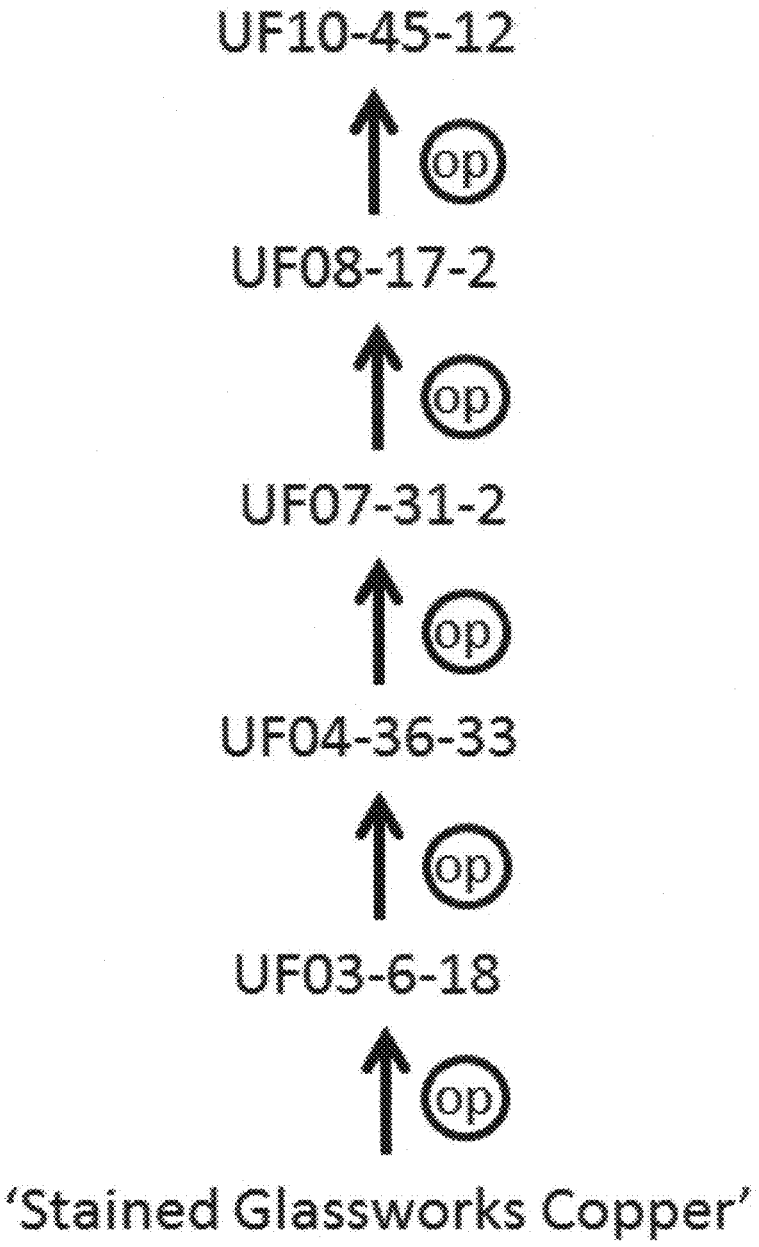
FIG. 1—shows the pedigree of the claimed plant.
Figure 2:
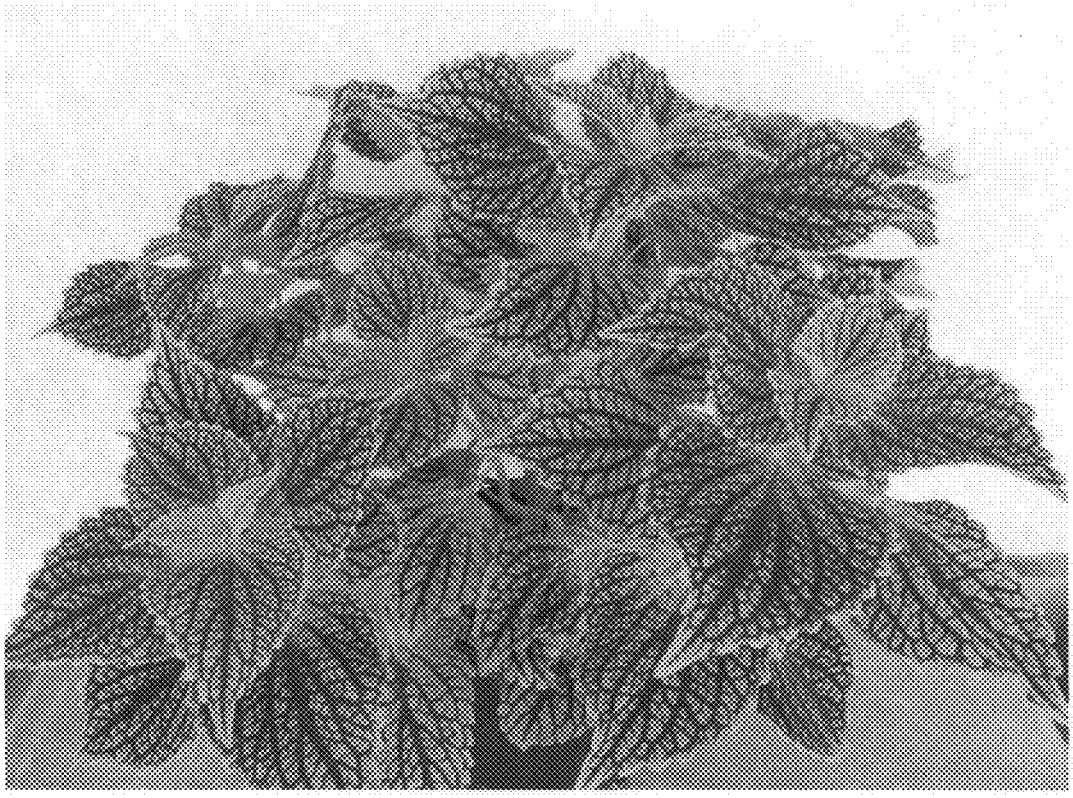
FIGS. 2 and 3 were taken of 9-week-old plants grown from cuttings in 1-gallon pots during September-November 2013 in greenhouses in Gainesville, Fla.
Figure 3:
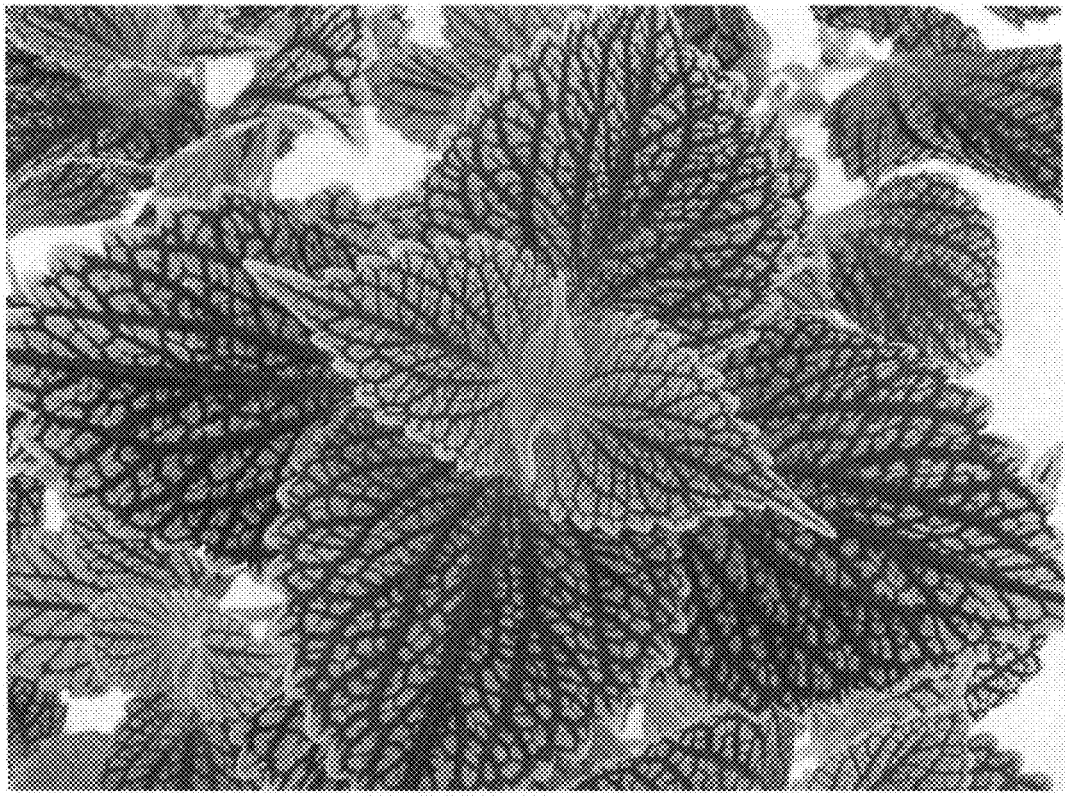

The following detailed description sets forth the distinctive characteristics of coleus variety 'UF10-45-12'. The detailed description was obtained using 9-week-old plants from cuttings growing in a glass greenhouse in Gainesville, Fla. in late fall 2013. The plants were pinched 2 weeks after cuttings were rooted, then grown in 1-gallon pots for approximately 9 weeks. Color references are to The R.H.S. Colour Chart of The Royal Horticultural Society of London (R.H.S.), 2007 5th Edition.

Classification:

*Family*.—Lamiaceae.

*Botanical*.—*Solenostemon scutellarioides*.

*Common name*.—Coleus.

*Cultivar name*.—'UF10-45-12'.

Parentage:

*Female parent*.—'UF08-17-2'.

*Male parent*.—Open-pollinated.

Plant description:

*Form*.—Spreading.

*Habit*.—Upright.

*Height* (*from top of soil*).—32-34 cm.

*Width* (*horizontal plant diameter*).—46-50 cm.

Propagation:

*Type cuttings*.—Vegetative meristems having at least 1 node.

*Time to initiate roots*.—3-4 days.

*Time to produce a rooted cutting*.—7-10 days.

*Root habit*.—Fibrous.

*Root description*.—Callus forms in 2 to 3 days, roots initiate in 3-4 days and become a highly branched cutting in 7-10 days.

Branches:

*Quantity per plant*.—6 to 8 main branches per plant with numerous side branches, pinched once.

*Branch color*.—RHS 145A.

*Texture*.—Smooth.

*Pubescence*.—Non-descript.

*Stem description*.—Square-shaped stem, 1.5 cm in diameter at the soil line.

*Branch diameter*.—0.5-0.6 cm at the base of a 26-cm-long branch.

*Branch length*.—26 cm.

*Internode length*.—4-5 cm.

*Anthocyanin*.—N/A.

Leaves:

*Quantity of leaves per branch*.—14 to 16. Arrangement: Opposite.

*Fragrance*.—Not fragrant.

*Shape*.—Deltoid.

*Length*.—11-13 cm.

*Width*.—8-10 cm.

*Apex*.—Narrowly acuminate.

*Base*.—Attenuate.

*Margin*.—Sinuate.

*Leaf texture* (*both surfaces*).—Slightly pubescent upper surface; smooth lower surface.

*Pubescence color* (*both surfaces*).—Non-descript with naked eye.

*Venation color*.—Upper surface: RHS 59A. Lower surface: RHS 145A.

*Venation pattern*.—Upper surface: Reticulate. Lower surface: Reticulate.

*Color*.—Immature leaf: Upper surface: RHS N144B background, with defined RHS 59A leaf veins. Lower surface: RHS 144A background, with defined RHS 145A leaf veins.

*Color*.—Mature leaf: Upper surface: RHS 144A background, with defined RHS 59A leaf veins. Lower surface: RHS 144B background, with defined RHS 145A leaf veins.

*Petiole length*.—4-5 cm.

*Petiole diameter*.—0.2-0.3 cm.

*Petiole color*.—RHS N144C.

*Petiole texture*.—Smooth, no pubescence.

Flowers and seeds: Flowers and seeds have not been observed.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Fla. have been long-tailed or citrus mealybugs (*Pseudococcus* sp.), which occur on older stock plant material held in the greenhouse for over 3-4 months. Impatiens Necrotic Spot Virus (*Bunyaviridae*) has also been observed in plants confined in greenhouses with mixed crops (peppers) infected with Western flower thrips (*Frankliniella occidentalis*). The most common pathogen of this species in the U.S. is downy mildew (*Peronospora lamii*). This pathogen has been observed in stock materials grown closely together in cooler growing seasons.

What is claimed is:

1. A new and distinct variety of *Solenostemon scutellarioides* plant called 'UF10-45-12' as shown and described herein.

* * * * *